United States Patent
Dubief

(10) Patent No.: US 10,272,170 B2
(45) Date of Patent: Apr. 30, 2019

(54) AEROSOL GENERATING DEVICE WITH AIR FLOW NOZZLES

(71) Applicant: Philip Morris Products S.A., Neuchatel (CH)

(72) Inventor: Flavien Dubief, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 701 days.

(21) Appl. No.: 14/361,568

(22) PCT Filed: Dec. 5, 2012

(86) PCT No.: PCT/EP2012/074518
§ 371 (c)(1),
(2) Date: May 29, 2014

(87) PCT Pub. No.: WO2013/083638
PCT Pub. Date: Jun. 13, 2013

(65) Prior Publication Data
US 2014/0334802 A1 Nov. 13, 2014

(30) Foreign Application Priority Data
Dec. 8, 2011 (EP) .................................. 11192698

(51) Int. Cl.
*A61M 16/00* (2006.01)
*A61H 33/12* (2006.01)
(Continued)

(52) U.S. Cl.
CPC .............. *A61L 9/03* (2013.01); *A24F 47/008* (2013.01)

(58) Field of Classification Search
CPC .................................. A61L 9/03; A24F 47/008
(Continued)

(56) References Cited

U.S. PATENT DOCUMENTS 5,144,962 A * 9/1992 Counts .................. A24F 47/008
 128/200.14
5,894,841 A * 4/1999 Voges .................... A24F 47/008
 128/200.14

(Continued)

FOREIGN PATENT DOCUMENTS

| CN | 201079011 Y | 7/2008 |
| CN | 101351128 A | 1/2009 |

(Continued)

OTHER PUBLICATIONS

Combined Chinese Office Action and Search Report dated Nov. 3, 2015 in Patent Application No. 201280059776.X (with English language translation).

(Continued)

*Primary Examiner* — Thor S Campbell
(74) *Attorney, Agent, or Firm* — Oblon, McClelland, Maier & Neustadt, L.L.P.

(57) ABSTRACT

There is provided an aerosol generating device, including a vaporizer for heating an aerosol-forming substrate to form an aerosol; a plurality of air flow nozzles; and at least one air outlet. The air flow nozzles and the air outlet are arranged to define an air flow route between the air flow nozzles and the air outlet. Each of the air flow nozzles includes an aperture arranged to direct air towards the vicinity of the vaporizer in a direction across the surface of the vaporizer so as to manage particle size in the aerosol.

13 Claims, 2 Drawing Sheets

(51) Int. Cl.
*A61L 9/03* (2006.01)
*A24F 47/00* (2006.01)

(58) Field of Classification Search
USPC ............... 392/386, 390, 396–398, 402–404
See application file for complete search history.

(56) References Cited

U.S. PATENT DOCUMENTS

| | | | | |
|---|---|---|---|---|
| 6,196,218 | B1* | 3/2001 | Voges | A24F 47/002 |
| | | | | 128/200.14 |
| 6,598,607 | B2* | 7/2003 | Adiga | A24F 47/004 |
| | | | | 131/194 |
| 2005/0016550 | A1* | 1/2005 | Katase | A24F 47/002 |
| | | | | 131/194 |
| 2007/0267031 | A1 | 11/2007 | Hon | |
| 2008/0047571 | A1* | 2/2008 | Braunshteyn | A24D 3/045 |
| | | | | 131/202 |
| 2008/0276947 | A1 | 11/2008 | Martzel | |
| 2009/0095311 | A1 | 4/2009 | Han | |
| 2009/0126745 | A1 | 5/2009 | Hon | |
| 2009/0188490 | A1* | 7/2009 | Han | A61M 11/041 |
| | | | | 128/200.14 |
| 2011/0094523 | A1 | 4/2011 | Thorens et al. | |
| 2011/0168194 | A1 | 7/2011 | Hon | |
| 2011/0209717 | A1 | 9/2011 | Han | |
| 2011/0277757 | A1* | 11/2011 | Terry | A24F 47/008 |
| | | | | 128/202.21 |
| 2012/0285476 | A1 | 11/2012 | Hon | |

FOREIGN PATENT DOCUMENTS

| | | |
|---|---|---|
| DE | 10 2006 004 484 | 8/2007 |
| EP | 1 736 065 | 12/2006 |
| EP | 2 022 349 | 2/2009 |
| EP | 2 319 334 | 5/2011 |
| GB | 2 468 512 | 9/2010 |
| JP | 2007-532118 A | 11/2007 |
| JP | 2009-537119 A | 10/2009 |
| JP | 2011-518567 A | 6/2011 |
| WO | WO 2007/078273 A1 | 7/2007 |
| WO | WO 2011/050943 A1 | 5/2011 |

OTHER PUBLICATIONS

International Preliminary Report on Patentability dated Jun. 10, 2014 in PCT/EP2012/074518.
Extended European Search Report dated May 11, 2012 in Patent Application No. 11192698.6.
Written Opinion of the International Searching Authority dated Apr. 26, 2013 in PCT/EP12/074518 Filed Dec. 5, 2012.
International Search Report dated Apr. 26, 2013 in PCT/EP12/074518 Filed Dec. 5, 2012.
Office Action dated Sep. 20, 2016 in Taiwanese Patent Application No. 101145954 (with English translation).
Office Action dated Sep. 15, 2016 in Russian Patent Application No. 2014127684 (with English language translation).
Office Action dated Oct. 3, 2016 in Japanese Patent Application No. 2014-545245 (with English language translation).

* cited by examiner

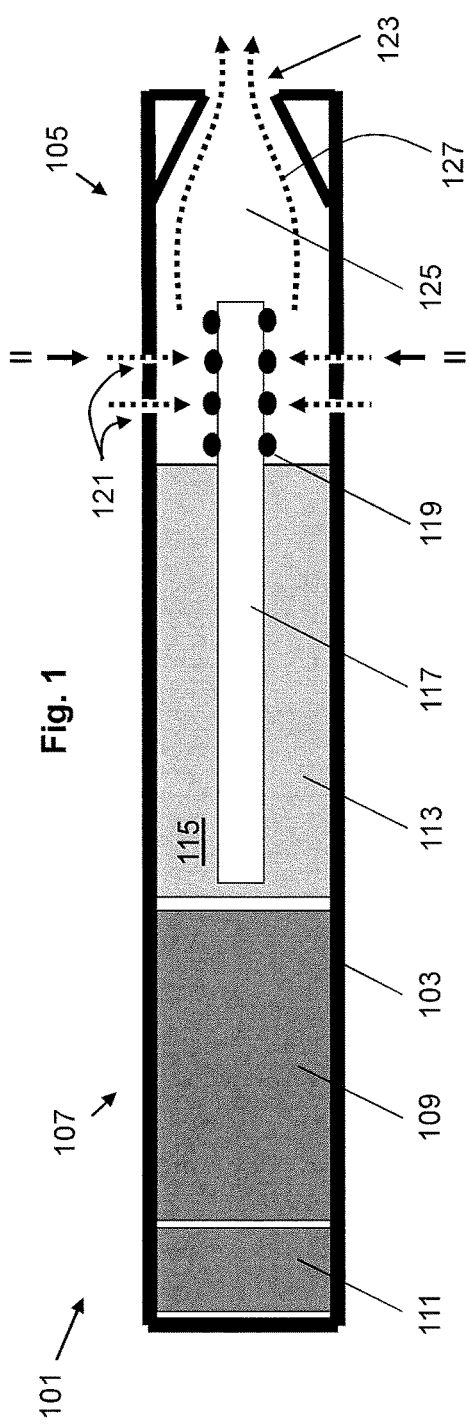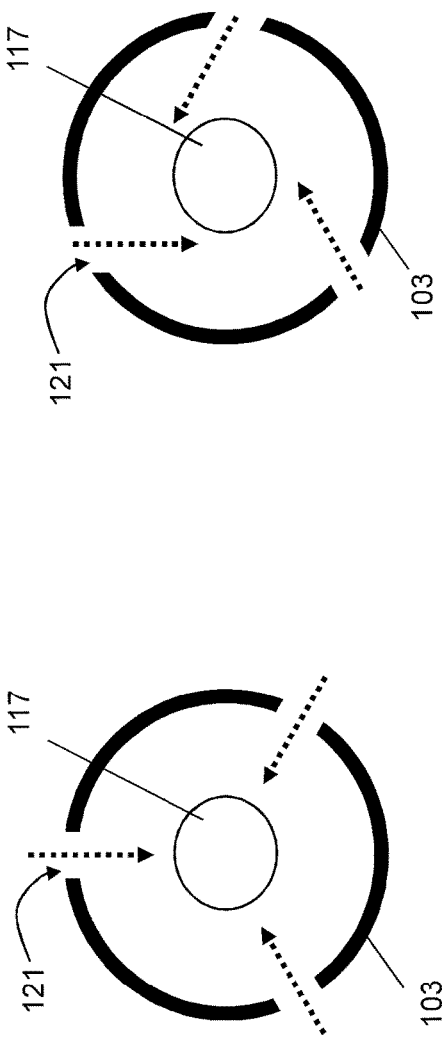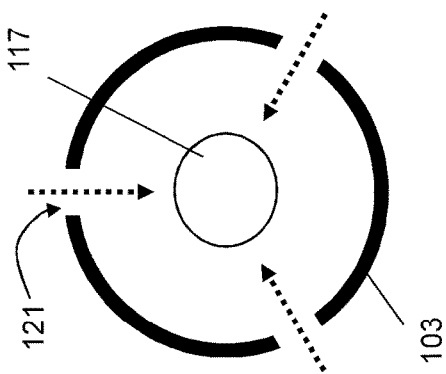

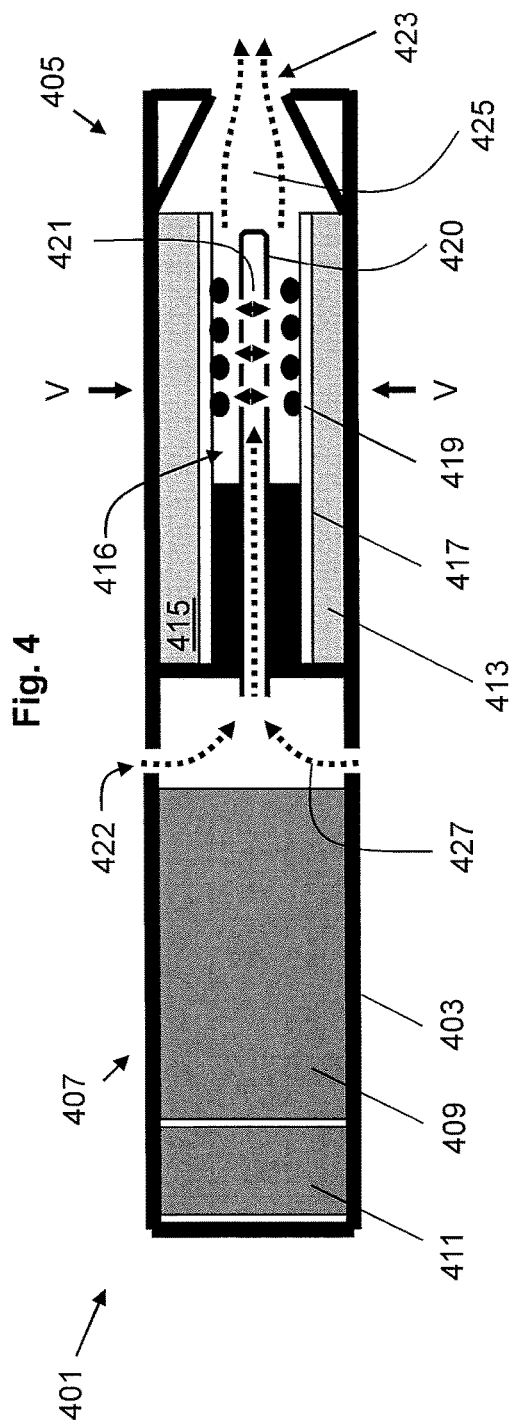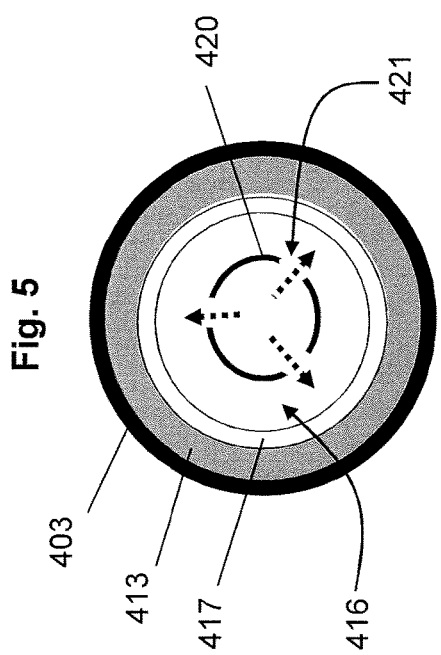

AEROSOL GENERATING DEVICE WITH AIR FLOW NOZZLES

CROSS REFERENCE TO RELATED APPLICATION

This application is a national phase application based on PCT/EP2012/074518, filed on Dec. 5, 2012.

The present invention relates to an aerosol generating device for heating an aerosol-forming substrate. Particularly, but not exclusively, the present invention relates to an electrically operated aerosol generating device for heating a liquid aerosol-forming substrate.

WO-A-2009/132793 discloses an electrically heated smoking system. A liquid is stored in a liquid storage portion, and a capillary wick has a first end which extends into the liquid storage portion for contact with the liquid therein, and a second end which extends out of the liquid storage portion. A heating element heats the second end of the capillary wick. The heating element is in the form of a spirally wound electric heating element in electrical connection with a power supply, and surrounding the second end of the capillary wick. In use, the heating element may be activated by the user to switch on the power supply. Suction on a mouthpiece by the user causes air to be drawn into the electrically heated smoking system over the capillary wick and heating element and subsequently into the mouth of the user.

It is an object of the present invention to improve the generation of aerosol in an aerosol generation device or system.

According to one aspect of the invention, there is provided an aerosol generating device comprising: a vaporizer for heating an aerosol-forming substrate; a plurality of air flow vents; and at least one air outlet, the air flow vents and the air outlet being arranged to define an air flow route between the air flow vents and the air outlet; and wherein each of the plurality of air flow vents comprises an aperture arranged to direct air towards the vicinity of the vaporizer so as to manage particle size in the aerosol.

According to another aspect of the invention, there is provided a cartridge comprising: a storage portion for storing an aerosol-forming substrate; a vaporizer for heating the aerosol-forming substrate; a plurality of air flow vents; and at least one air outlet, the air flow vents and the air outlet being arranged, to define an air flow route between the air flow vents and the air outlet; wherein each of the plurality of air flow vents comprises an aperture arranged to direct air towards the vicinity of the vaporizer so as to manage particle size in the aerosol.

The aerosol generating device and cartridge cooperate to provide an aerosol generating system for heating an aerosol-forming substrate. The cartridge or aerosol generating device may comprise a storage portion for storing the aerosol-forming substrate. The vaporizer may be contained in the aerosol generating device. The vaporizer may also be contained in the cartridge. The plurality of air flow vents may be provided in either the aerosol generating device or in the cartridge, or some of the plurality of air flow vents may be provided in the aerosol generating device and other of the plurality of air flow vents may be provided in the cartridge. The air outlet may be provided in either the aerosol generating device or in the cartridge or, if more than one air outlet is provided, one or more air outlets may be provided in the aerosol generating device and one or more air outlets may be provided in the cartridge.

According to another aspect of the invention, there is provided an aerosol generating system comprising: a vaporizer for heating an aerosol-forming substrate; a plurality of air flow vents; and at least one air outlet, the air flow vents and the air outlet being arranged to define an air flow route between the air flow vents and the air outlet; wherein each of the plurality of air flow vents comprises an aperture arranged to direct air towards the vicinity of the vaporizer so as to manage particle size in the aerosol, wherein the air flow vents direct the air towards the vicinity of the vaporizer in more than one direction.

For all aspects of the invention, the storage portion may be a liquid storage portion. For all aspects of the invention, the aerosol forming substrate may be a liquid aerosol forming substrate. The aerosol-forming substrate may contain nicotine. The aerosol-forming substrate may be adsorbed, coated, impregnated or otherwise loaded onto a carrier or support.

The aerosol-forming substrate may alternatively be any other sort of substrate, for example, a gas substrate or a gel substrate, or any combination of the various types of substrate. The aerosol-forming substrate may be a solid substrate.

The vaporizer of the aerosol generating device or system is arranged to heat the aerosol-forming substrate to form a supersaturated vapour. The supersaturated vapour is mixed with and carried in the air flow from the plurality of air flow nozzles towards the air outlet. The vapour condenses to form an aerosol, which is carried towards the air outlet into the mouth of a user. The aerosol generating device or cartridge may further comprise an aerosol forming chamber in the air flow route between the plurality of air flow nozzles and the air outlet. The aerosol forming chamber may assist or facilitate the generation of the aerosol. The aerosol generating device may include the aerosol-forming substrate or may be adapted to receive the aerosol-forming substrate. As known to those skilled in the art, an aerosol is a suspension of solid particles or liquid droplets in a gas, such as air.

Each air flow vent comprises a small aperture, orifice or hole. Each air flow vent may also comprise a nozzle. The small size of the aperture, orifice or hole results in a high velocity air flow through the air flow vent or vent or nozzle. This is because air flow speed may be increased by decreasing the cross sectional area of the air flow path, so as to take advantage of the Venturi effect. That is, the velocity of the air flow increases as the cross sectional area decreases and the air flow through a constricted cross section increases in speed. Each air flow vent or nozzle is arranged to propel, drive or force high velocity air towards the vicinity of the vaporizer. For the cartridge, the air flow vent or nozzles direct the air towards the vicinity of the vaporizer in more than one direction. For the device, the air flow vent or nozzles direct the air towards the vicinity of the vaporizer in more than one direction. The high speed air flow affects the cooling rate of the supersaturated vapour which affects the formation of the aerosol. This, in turn, affects the mean particle size and the particle size distribution of the aerosol. Preferably, the distance between the air flow vent or nozzles and the vaporizer is small. This improves control of the air flow velocity, since there is little opportunity for deceleration of the incoming air or the formation of complex turbulence patterns in the air flow. Because the air flow vent or nozzles direct the air towards the vicinity of the vaporizer in more than one direction, the air flow in the vicinity of the vaporizer is relatively homogeneous. Moreover, the cooling rate on all sides of the vaporizer is substantially equal, which results in a small particle size distribution of the aerosol.

Thus, the invention provides a number of advantages. First, the increased cooling rate results in a smaller mean droplet size in the aerosol. This results in a better sensory experience for the user. Second, the homogeneous air flow results in a smaller range of particle sizes in the aerosol. This results in a more consistent aerosol, which results in a more consistent experience for the user. Third, by increasing the cooling rate, the process of producing the aerosol is accelerated. This means that the aerosol generating device and cartridge can be made smaller, since a reduced air flow length is required for the aerosol formation. The invention allows all three advantages to be realised. Moreover, high velocity air flow may also reduce the amount of condensation that is able to form within the aerosol generating device and cartridge, particularly within the aerosol forming chamber. Formation of condensation may affect liquid leakage from the aerosol generating device and cartridge. Thus, a further advantage of the invention is that it can be used to reduce liquid leakage.

In one embodiment, the air flow vent or nozzles comprise air inlet vents or nozzles. That is to say, the air flow vent or nozzles provide the first (furthest upstream) conduit for ambient air to be drawn into the aerosol generating device or cartridge. In that embodiment, preferably the length of the air inlet vent or nozzles is minimised, so that ambient air is drawn as directly as possible from outside the aerosol generating device or cartridge towards the vicinity of the vaporizer. This improves control of the air flow velocity, since there is little opportunity for deceleration of the air flow or for the creation of complex turbulence patterns. In that embodiment, preferably the air inlet vent or nozzles are provided in a housing of the aerosol generating device or cartridge.

Alternatively, however, the air flow vent or nozzles may not comprise air inlet vent or nozzles. In that embodiment, conduits further upstream of the air flow vent or nozzles provide inlets for ambient air to be drawn into the aerosol generating device or cartridge. The air flow vent or nozzles simply channel the air towards the vicinity of the vaporizer at a high velocity. This allows control of the velocity in the vicinity of the vaporizer, whilst also allowing the invention to be compatible with various designs of aerosol generating device or cartridge or system.

In one embodiment, at least one of the air flow vent or nozzles includes a deviating portion. The crooked portion may comprise a crooked or angled portion. The deviating portion may be curved. The deviating portion may be provided in one, some or all of the air flow vent or nozzles. This is particularly advantageous if the air flow vent or nozzles comprise air inlet vent or nozzles, and particularly if the air flow vent or nozzles are provided in a housing of the aerosol generating device or cartridge. It may then be possible for a user to see the vaporizer or other components in the aerosol generating device or cartridge and potentially access and tamper with the vaporizer or other components. Including a deviating portion in the air flow vent or nozzles prevents access to the internal components of the aerosol generating device or cartridge or system.

In one embodiment, the air flow vent or nozzles are arranged, when the device is in use with the cartridge to direct the air towards the vicinity of the vaporizer in a direction across the surface of the vaporizer. This air flow direction may be advantageous as it provides a high velocity air flow generally parallel to the surface of the vaporizer. This may increase the speed of the process of vaporization. In addition, in some embodiments, this air flow direction creates a swirling air flow, that is to say, a twisting, rotating or spiralling air flow, in the vicinity of the vaporizer. This has been found to increase the cooling rate, which decreases the mean particle size in the aerosol. In addition, if the vaporizer comprises a heater, directing the air across the surface of the vaporizer, rather than directly onto the vaporizer reduces unnecessary cooling of the heater. In one embodiment, the flow nozzles are arranged to direct the air along a path spaced a predetermined distance from the surface of the vaporiser rather than directly at the vaporiser. This prevents the high speed air from significantly cooling the vaporiser but rapidly cools vapour that has moved away from the vaporiser. This improves the efficiency of the aerosol generating device.

Since the air flow vent or nozzles direct the high velocity air in more than one direction, the air may be directed across the surface of the vaporizer at more than one portion of the vaporizer. This increases the likelihood of substantially equal cooling on all sides of the vaporizer, which leads to consistent aerosol formation. This also enhances the swirl effect of the air flow, which increases the cooling rate.

Alternatively, the air flow vent or nozzles may be arranged to direct the air towards the vicinity of the vaporizer directly onto the surface of the vaporizer. This air flow direction may be directed substantially perpendicular to the surface of the vaporizer. This air flow direction may be advantageous because it increases the cooling rate, which decreases the mean particle size in the aerosol.

Since the air flow vent or nozzles direct the high the high velocity air in more than one direction, the air may be directed onto more than one portion of the vaporizer. This increases the cooling rate and also increases the likelihood of substantially equal cooling on all sides of the vaporizer.

The air flow vent or nozzles may direct the high velocity air towards the vicinity of the vaporizer in any other desired direction or directions. For example, the air flow vent or nozzles may direct the air in the longitudinal direction of the aerosol generating device or cartridge. Moreover, each air flow vent or nozzle may direct the air in its own respective direction. For example, one air flow vent or nozzle may direct the high velocity air across the surface of the vaporizer and another air flow vent or nozzle may direct the air directly onto the surface of vaporizer.

Any suitable number of air flow vent or nozzles may be provided. The air flow vent or nozzles may have any suitable cross sectional area or diameter which results in the desired air flow velocity in the vicinity of the vaporizer. The vent or nozzles' cross sectional area and diameter will also affect the resistance to draw. The vent or nozzles may have the same or different cross sectional areas and diameters. The vent or nozzles may also have any desired cross sectional shape and the vent or nozzles may have the same or different cross sectional shapes. Advantageously, each of the air flow vents has a diameter of less than or approximately equal to 0.4 mm. This provides high speed, directed air flow. In one embodiment, for a flow rate of 27.5 milliliters per second through the air outlet, the air flow velocity through each of the air flow vents is between 10 and 30 meters per second. The separation of the air flow vent or nozzles and the vaporizer may be set according to the desired cooling rate in the aerosol generating device. The vent or nozzle-vaporizer separation may also affect the resistance to draw. The vent or nozzles may be separated from the vaporizer by the same or different distances. The air flow vent or nozzles may direct the air flow in any direction which results in the desired air flow patterns in the aerosol generating device or cartridge. The vent or nozzles may direct the air flow in the same or in different directions.

The air flow vent or nozzles may be arranged in any suitable pattern which results in the desired cooling rate. Preferably, the air flow vent or nozzles are arranged symmetrically with respect to the vaporizer. This results in a homogenous air flow around the vaporizer, which results in a consistent cooling rate and hence a consistent particle size in the aerosol. Preferably, the air flow vent or nozzles are arranged symmetrically with respect to the longitudinal axis of the aerosol generating device or cartridge. The vent or nozzles may be arranged in a plurality of sets of vent or nozzles. Each set may be longitudinally spaced from other sets. However, one, two, three, four or more sets of longitudinally spaced vent or nozzles may be provided, and each set may comprise one, two, three, four or more air flow vent or nozzles.

If the air flow vent or nozzles are provided on a housing of the aerosol generating device or cartridge, the air flow vent or nozzles may be circumferentially spaced around the housing. Preferably, the air flow vent or nozzles are symmetrically spaced around the housing so as to increase the likelihood that the cooling rate is substantially equal throughout the aerosol generating device and cartridge. The vent or nozzles may be arranged in one or more rows longitudinally spaced along the housing. In one embodiment, two longitudinally spaced sets of air flow vent or nozzles are provided on the housing, and each set comprises three air flow vent or nozzles symmetrically spaced around the circumference of the housing.

In one embodiment, the aerosol generating device or cartridge further comprises: a liquid storage portion for storing the liquid aerosol-forming substrate; and an elongate capillary body for conveying the liquid aerosol-forming substrate from the liquid storage portion towards the vaporizer, the capillary body having a first end extending into the liquid storage portion and a second end opposite the first end, wherein the vaporizer is arranged to heat the liquid aerosol-forming substrate in the second end of the capillary body.

In this embodiment, in use, liquid is transferred from the liquid storage portion by capillary action from the first end of the capillary body towards the second end of the capillary body. Liquid in the second end of the capillary body is vaporized to form the supersaturated vapour. Preferably, the capillary body is in contact with liquid aerosol-forming substrate in the liquid storage portion. The liquid aerosol-forming substrate has suitable physical properties, including but not limited to surface tension, viscosity, density, thermal conductivity, boiling point and vapour pressure, which allow the liquid to be transported through the capillary body by capillary action.

In this embodiment, preferably the air flow vent or nozzles comprise air inlet vent or nozzles. That is to say, the air flow vent or nozzles provide the first (furthest upstream) conduit for ambient air to be drawn into the aerosol generating device or cartridge. Preferably, the air inlet vent or nozzles are provided in a housing of the aerosol generating device or cartridge. Preferably, the air inlet vent or nozzles are provided in the housing of the aerosol generating device or cartridge in the vicinity of the second end of the capillary body and vaporizer, so that ambient air is drawn directly from outside the aerosol generating device or cartridge towards the vicinity of the second end of the capillary body and the vaporizer.

In this embodiment, if the air flow vent or nozzles are arranged to direct the air towards the vicinity of the vaporizer in a direction across the surface of the vaporizer, the air flow vent or nozzles may be arranged to direct the air across the surface of the capillary body. This is advantageous as it avoids excessive drying of the capillary body. The elongate capillary body preferably extends along the longitudinal axis of the aerosol generating device. If the aerosol generating device or cartridge or both device and cartridge have a circular cross section, the elongate capillary body preferably extends generally along the central axis of the aerosol generating device or cartridge. In that case, the direction of the air across the surface of the capillary body may be in a tangential direction relative to the capillary body and the circular cross section of the aerosol generating device or cartridge and the nozzles may be arranged to direct the air along a path a predetermined distance from the capillary body at its closest point, i.e. at a predetermined altitude above the surface of the capillary body. The air flow may be substantially perpendicular to the longitudinal axis. Alternatively, the air flow vent or nozzles may be arranged to direct the air across the surface of the vaporizer but directly onto the surface of the capillary body.

In this embodiment, if the air flow vent or nozzles are arranged to direct the air towards the vicinity of the vaporizer directly onto the surface of the vaporizer, the air flow vent or nozzles may be arranged to direct the air directly onto the surface of the capillary body. The elongate capillary body preferably extends along the longitudinal axis of the aerosol generating device or cartridge. If the aerosol generating device or cartridge or both device and cartridge have a circular cross section, the elongate capillary body preferably extends generally along the central axis of the aerosol generating device or cartridge. In that case, the direction of the air directly onto the surface of the capillary body may be in a radial direction relative to the capillary body and the circular cross section of the aerosol generating device or cartridge. The air flow may be substantially perpendicular to the longitudinal axis. Alternatively, the air flow vent or nozzles may be arranged to direct the air directly onto the surface of the capillary body but not directly onto the vaporizer. For example, the air flow vent or nozzles may direct the air directly onto a portion of the capillary body adjacent the vaporizer. This is particularly advantageous if the vaporizer comprises a heater because this reduces cooling of the heater.

If the air flow vent or nozzles are provided on a housing of the aerosol generating device or cartridge, the air flow vent or nozzles may be circumferentially spaced around the housing. Preferably, the air flow vent or nozzles are symmetrically spaced around the housing so as to increase the likelihood that the cooling rate is substantially equal throughout the aerosol generating device. The elongate capillary body preferably extends along the central longitudinal axis of the aerosol generating device or cartridge. Thus, if the air flow vent or nozzles are symmetrically spaced around the housing, this will result in a substantially equal air flow on all sides of the capillary body. The vent or nozzles may be arranged in one or more rows longitudinally spaced along the housing. In one embodiment, two longitudinally spaced sets of air flow vent or nozzles are provided on the housing, and each set comprises three air flow vent or nozzles symmetrically spaced around the circumference of the housing. Other numbers and layouts of air flow vent or nozzles are of course possible, however.

The capillary body may comprise any suitable material or combination of materials which is able to convey the liquid aerosol-forming substrate towards the vaporizer. The capillary body preferably comprises a porous material, but this need not be the case. The capillary body may have the form of a wick. The capillary body may have a fibrous or spongy structure. The capillary body preferably comprises a bundle of capillaries. For example, the capillary body may comprise a plurality of fibres or threads or other fine bore tubes and these may be generally aligned in the longitudinal direction of the aerosol generating device or system. Alternatively, the capillary body may comprise sponge-like or foam-like material formed into a rod shape. The rod shape may extend generally along the longitudinal direction of the aerosol generating device or system. The particular preferred capillary material or materials will depend on the physical properties of the liquid aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity so as to be used with different liquid physical properties.

The liquid storage portion may protect the liquid aerosol-forming substrate from ambient air (because air cannot generally enter the liquid storage portion). The liquid storage portion may protect the liquid aerosol-forming substrate from light, so that the risk of degradation of the liquid is significantly reduced. Moreover, a high level of hygiene can be maintained. The liquid storage portion may not be refillable. Thus, when the liquid aerosol-forming substrate in the liquid storage portion has been used up, the cartridge is replaced. Alternatively, the liquid storage portion may be refillable. In that case, the cartridge may be replaced after a certain number of refills of the liquid storage portion. Preferably, the liquid storage portion is arranged to hold liquid aerosol-forming substrate for a pre-determined number of puffs.

In another embodiment, the liquid storage portion includes an interior passageway, wherein the vaporizer extends through at least part of the interior passageway when the device is in use with the cartridge; and the cartridge further comprises a capillary interface at least partially lining the interior passageway for conveying the liquid aerosol-forming substrate towards the vaporizer.

In this embodiment, in use, liquid is transferred from the liquid storage portion by capillary action through the capillary interface lining the interior passageway. A first face of the capillary interface is preferably in contact with liquid aerosol-forming substrate in the liquid storage portion. A second face of the capillary interface is in contact with or adjacent the vaporizer. Liquid near the second face of the capillary interface is vaporized to form the supersaturated vapour, which is mixed with and carried in the air flow through the interior passageway. The interior passageway of the liquid storage portion may comprise an aerosol forming chamber for facilitating generation of the aerosol. The liquid storage portion may have a cylindrical shape and the interior passageway may extend along the longitudinal axis of the cylinder. Thus, the liquid storage portion may have an annular cross section. The liquid aerosol-forming substrate has physical properties, including but not limited to surface tension, viscosity, density, thermal conductivity, boiling point and vapour pressure, which allow the liquid to be transported through the capillary interface by capillary action.

In this embodiment, if the air flow vent or nozzles are arranged to direct the air towards the vicinity of the vaporizer directly onto the surface of the vaporizer, the air flow vent or nozzles may be arranged to direct the air directly onto the surface of the capillary interface. The interior passageway of the liquid storage portion preferably extends along the longitudinal axis of the cartridge. The capillary interface also preferably extends along the longitudinal axis of the cartridge. If the cartridge has a circular cross section, the interior passageway and capillary interface are preferably centred on the central axis of the cartridge. In that case, the direction of the air directly onto the surface of the capillary interface may be in a radial direction relative to the interior passageway, capillary interface and the circular cross section of the cartridge. The air flow may be substantially perpendicular to the longitudinal axis. Alternatively, the air flow vent or nozzles may be arranged to direct the air directly onto the surface of the capillary interface but not directly onto the vaporizer. For example, the air flow vent or nozzles may direct the air directly onto a portion of the capillary interface adjacent the vaporizer.

The capillary interface may comprise any suitable material or combination of materials which is able to convey the liquid aerosol-forming substrate towards the vaporizer. The capillary interface preferably comprises a porous material, but this need not be the case. The capillary interface may comprise any suitable capillary material formed into a tube shape. The tube of capillary material may extend along all or part of the length of the interior passageway in the liquid storage portion. The capillary interface may have a fibrous or spongy structure. The capillary interface may comprise a plurality of fibres or threads or other fine bore tubes. Alternatively, the capillary interface may comprise sponge-like or foam-like material. The particular preferred capillary material or materials will depend on the physical properties of the liquid aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity so as to be used with different liquid physical properties.

The liquid storage portion may protect the liquid aerosol-forming substrate from ambient air (because air cannot generally enter the liquid storage portion). The liquid storage portion may protect the liquid aerosol-forming substrate from light, so that the risk of degradation of the liquid is significantly reduced. Moreover, a high level of hygiene can be maintained. The liquid storage portion may not be refillable. Thus, when the liquid aerosol-forming substrate in the liquid storage portion has been used up, the cartridge is replaced. Alternatively, the liquid storage portion may be refillable. In that case, the cartridge may be replaced after a certain number of refills of the liquid storage portion. Preferably, the liquid storage portion is arranged to hold liquid aerosol-forming substrate for a pre-determined number of puffs.

In another embodiment, the device or cartridge may further comprise an air inlet pipe at least partially extending into the interior passageway, wherein the air inlet pipe includes the plurality of air flow vent or nozzles and the air flow route extends along the air inlet pipe, through the air flow vent or nozzles and to the air outlet.

The air flow vent or nozzles may be circumferentially spaced around the air inlet pipe. Preferably, the air flow vent or nozzles are symmetrically spaced around the air inlet pipe so as to increase the likelihood that the cooling rate is substantially equal throughout the aerosol generating device or system. The interior passageway of the liquid storage portion and the capillary interface preferably extends along the central longitudinal axis of the cartridge. The air inlet pipe also preferably extends along the central longitudinal axis of the cartridge. Thus, if the air flow vent or nozzles are symmetrically spaced around the air inlet pipe, this will result in a substantially equal air flow at all portions of the capillary interface and vaporizer. The vent or nozzles may be arranged in one or more rows longitudinally spaced along the air inlet pipe. In one embodiment, three longitudinally spaced sets of air flow vent or nozzles are provided on the air inlet pipe, and each set comprises three air flow vent or nozzles symmetrically spaced around the circumference of the air inlet pipe. Other numbers and layouts of air flow vent or nozzles are of course possible, however.

The aerosol generating device or cartridge may further comprise an air inlet and an air flow sensor for measuring air flow through the air inlet, wherein a secondary air flow route is defined between the air inlet and the air outlet. In this embodiment, the primary air flow is through the air flow vent or nozzles, but there is a secondary air flow through the air inlet. Preferably, the secondary air flow is small compared with the primary air flow. This allows the velocity through the air flow vent or nozzles in the primary air flow to be high but for the air velocity to be measured by the air flow sensor in the secondary air flow. The aerosol generating device or cartridge may be calibrated such that the air flow sensor in the secondary air flow route provides a measure of the air flow velocity in the primary air flow route, and particularly in the vicinity of the vaporizer. Preferably, the secondary air flow route bypasses the air flow vent or nozzles.

The vaporiser may be a heater. The heater may heat the aerosol-forming substrate means by one or more of conduction, convection and radiation. The heater may be an electric heater powered by an electric power supply. The heater may alternatively be powered by a non-electric power supply, such as a combustible fuel: for example, the heater may comprise a thermally conductive element that is heated by combustion of a gas fuel. The heater may heat the aerosol-forming substrate by means of conduction and may be at least partially in contact with the substrate, or a carrier on which the substrate is deposited. Alternatively, the heat from the heater may be conducted to the substrate by means of an intermediate heat conductive element. Alternatively, the heater may transfer heat to the incoming ambient air that is drawn through the aerosol-generating system during use, which in turn heats the aerosol-forming substrate by convection.

Preferably, the aerosol generating device is electrically operated and the vaporizer comprises an electric heater for heating the aerosol-forming substrate.

The electric heater may comprise a single heating element. Alternatively, the electric heater may comprise more than one heating element for example two, or three, or four, or five, or six or more heating elements. The heating element or heating elements may be arranged appropriately so as to most effectively heat the aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

Alternatively, the at least one electric heating element may comprise an infra-red heating element, a photonic source or an inductive heating element.

The at least one electric heating element may take any suitable form. For example, the at least one electric heating element may take the form of a heating blade. Alternatively, the at least one electric heating element may take the form of a casing or substrate having different electro-conductive portions, or an electrically resistive metallic tube. Alternatively, the at least one electric heating element may be a disk (end) heater or a combination of a disk heater with heating needles or rods. Alternatively, the at least one electric heating element may comprise a flexible sheet of material. Other alternatives include a heating wire or filament, for example a nickel-chromium, platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to heat the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material. Other suitable materials which release heat via a reversible phase change include paraffin, sodium acetate, naphthalene, wax, polyethylene oxide, a metal, metal salt, a mixture of eutectic salts or an alloy.

The heat sink may be arranged such that it is directly in contact with the aerosol-forming substrate and can transfer the stored heat directly to the aerosol-forming substrate. Alternatively, the heat stored in the heat sink or heat reservoir may be transferred to the aerosol-forming substrate by means of a heat conductor, such as a metallic tube.

The at least one heating element may heat the aerosol-forming substrate by means of conduction. The heating element may be at least partially in contact with the aerosol-forming substrate. Alternatively, the heat from the heating element may be conducted to the aerosol-forming substrate by means of a heat conductor element.

Alternatively, the at least one heating element may transfer heat to the incoming ambient air that is drawn through the aerosol generating device during use, which in turn heats the aerosol-forming substrate by convection. The ambient air may be heated before passing through the aerosol-forming substrate. Alternatively, the ambient air may be first drawn through the aerosol-forming substrate and then heated.

However, the invention is not limited to heater vaporizers but may be used in aerosol generating devices and systems in which the vapour and resulting aerosol is generated by a mechanical vaporizer, for example but not limited to a piezo vaporizer or an atomizer using pressurized liquid.

In a particularly preferred embodiment, the aerosol generating device is electrically operated, the vaporizer comprises an electric heater, and the aerosol generating device or cartridge further comprises: an elongate capillary body for conveying the liquid aerosol-forming substrate from the liquid storage portion towards the electric heater, the capillary body having a first end extending into the liquid storage portion and a second end opposite the first end, wherein the electric heater is arranged to heat the liquid aerosol-forming substrate in the second end of the capillary body. When the heater is activated, liquid in the second end of the capillary body is vaporized by the heater to form the supersaturated vapour.

In another particularly preferred embodiment, the aerosol generating device is electrically operated, the vaporizer comprises an electric heater, and the aerosol generating device further comprises: a first end having a mouthpiece; a second end opposite the first end; an electric power supply and electric circuitry for connecting to the electric heater; a storage portion for storing the liquid aerosol-forming substrate; and an elongate capillary body for conveying the liquid aerosol-forming substrate from the liquid storage portion towards the electric heater, the capillary body having a first portion extending into the liquid storage portion and a second portion opposite the first portion; wherein the electric heater is arranged to heat the liquid aerosol-forming substrate in the second portion of the capillary body; wherein the liquid storage portion, capillary body and electric heater are arranged in the first end of the aerosol generating device; and wherein the electric power supply and electric circuitry are arranged in the second end of the aerosol generating device. The liquid storage portion, and optionally the capillary body and the heater, may be removable from the aerosol generating device as a single component.

In another particularly preferred embodiment, the aerosol generating device is electrically operated and the vaporizer comprises an electric heater; the aerosol generating device comprises an electric power supply and electric circuitry for connecting to the electric heater; and the cartridge comprises a mouthpiece and an elongate capillary body for conveying the liquid aerosol-forming substrate from the liquid storage portion towards the electric heater, the capillary body having a first portion extending into the liquid storage portion and a second portion opposite the first portion, wherein the electric heater is provided in the cartridge and is arranged to heat the liquid aerosol-forming substrate in the second portion of the capillary body.

The liquid storage portion, and optionally the capillary body and the heater, may be removable from the aerosol generating system as a single component.

In another particularly preferred embodiment, the aerosol generating system is electrically operated, the vaporizer comprises an electric heater, and the liquid storage portion includes an interior passageway, wherein the electric heater extends through at least part of the interior passageway when the device is in use with the cartridge; and the device or cartridge further comprises a capillary interface at least partially lining the interior passageway when the device is in use with the heater for conveying the liquid aerosol-forming substrate towards the electric heater. When the heater is activated, liquid in the capillary interface is vaporized by the heater to form the supersaturated vapour.

In another particularly preferred embodiment, the aerosol generating device is electrically operated, the vaporizer comprises an electric heater and the liquid storage portion includes an interior passageway, wherein the electric heater extends through at least part of the interior passageway; the device comprises an electric power supply and electric circuitry for connecting to the electric heater; and the cartridge comprises a mouthpiece and a capillary interface at least partially lining the interior passageway for conveying the liquid aerosol-forming substrate towards the electric heater; wherein the electric heater is arranged in the cartridge.

The liquid storage portion and capillary interface, and optionally the heater, may be removable from the aerosol generating system as a single component.

The liquid aerosol-forming substrate preferably has physical properties, for example boiling point and vapour pressure, suitable for use in the aerosol generating device, cartridge or aerosol generating system. If the boiling point is too high, it may not be possible to heat the liquid but, if the boiling point is too low, the liquid may heat too readily. The liquid preferably comprises a tobacco-containing material comprising volatile tobacco flavour compounds which are released from the liquid upon heating. Alternatively, or in addition, the liquid may comprise a non-tobacco material. The liquid may include aqueous solutions, non-aqueous solvents such as ethanol, plant extracts, nicotine, natural or artificial flavours or any combination of these. Preferably, the liquid further comprises an aerosol former that facilitates the formation of a dense and stable aerosol. Examples of suitable aerosol formers are glycerine and propylene glycol.

The aerosol generating device or aerosol generating system may be electrically operated and may further comprise an electric power supply. The electric power supply may be an AC power source or a DC power source. Preferably, the electric power supply is a battery. The aerosol generating device or aerosol generating system may further comprise electric circuitry. In one embodiment, the electric circuitry comprises a sensor to detect air flow indicative of a user taking a puff. If an air inlet having an air flow sensor is provided as part of a secondary air flow route, the sensor may be provided in addition. In that case, preferably, the electric circuitry is arranged to provide an electric current pulse to the vaporizer when the sensor senses a user taking a puff. Preferably, the time-period of the electric current pulse is pre-set, depending on the amount of liquid desired to be vaporized. The electric circuitry is preferably programmable for this purpose. Alternatively, the electric circuitry may comprise a manually operable switch for a user to initiate a puff. The time-period of the electric current pulse is preferably pre-set depending on the amount of liquid desired to be vaporized. The electric circuitry is preferably programmable for this purpose.

Preferably, the aerosol generating device or cartridge or aerosol generating system comprises a housing. Preferably, the housing is elongate. If the aerosol generating device or cartridge includes an elongate capillary body, the longitudinal axis of the capillary body and the longitudinal axis of the housing may be substantially parallel. The housing may comprise a shell and a mouthpiece. In that case, all the components may be contained in either the shell or the mouthpiece. In one embodiment, the housing includes a removable insert. The removable insert may comprise the liquid storage portion, the capillary body and the vaporizer. Alternatively, the removable insert may comprise the liquid storage portion, the capillary interface and the vaporizer. In that embodiment, those parts of the aerosol generating device may be removable from the housing as a single component. This may be useful for refilling or replacing the liquid storage portion, for example.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the aerosol generating device and cartridge are portable, both individually and in cooperation. Preferably, the aerosol generating device is reusable by a user. Preferably, the cartridge is disposable by a user, for example when there is no more liquid contained in the liquid storage portion. The aerosol generating device and cartridge may cooperate to form an aerosol generating system which is a smoking system and which may have a size comparable to a conventional cigar or cigarette. The smoking system may have a total length between approximately 30 mm and approximately 150 mm. The smoking system may have an external diameter between approximately 5 mm and approximately 30 mm. In that embodiment, each air flow vent or nozzle may have a diameter less than or approximately equal to 0.4 mm. The aerosol produced by the aerosol generating system may have a mean particle size of less than approximately 1.5 microns or, more preferably, less than approximately 1.0 microns or, even more preferably, less than approximately 0.7 microns.

Preferably, the aerosol generating system is an electrically operated smoking system. According to the invention, there is provided an aerosol generating device comprising: a storage portion for storing aerosol-forming substrate; a vaporizer for heating the aerosol-forming substrate to form an aerosol; a plurality of air flow vent or nozzles; and at least one air outlet, the air flow vent or nozzles and the air outlet being arranged to define an air flow route between the air flow vent or nozzles and the air outlet; wherein each of the plurality of air flow vent or nozzles comprises an aperture arranged to direct air towards the vicinity of the vaporizer so as to manage particle size in the aerosol, wherein the air flow vent or nozzles direct the air towards the vicinity of the vaporizer in more than one direction.

Features described in relation to one aspect of the invention may be applicable to another aspect of the invention.

The invention will be further described, by way of example only, with reference to the accompanying drawings, of which:

FIG. 1 shows one embodiment of an aerosol generating system according to the invention;

FIG. 2 is a cross section along line II-II of FIG. 1;

FIG. 3 is an alternative cross section along line II-II of FIG. 1;

FIG. 4 shows another embodiment of an aerosol generating system according to the invention; and FIG. 5 is a cross section along line V-V of FIG. 4.

FIG. 1 is a schematic view of a first embodiment of an aerosol generating system according to the invention. FIG. 1 is schematic in nature. In particular, the components shown are not necessarily to scale either individually or relative to one another. Although not explicitly shown in FIG. 1, the aerosol generating system comprises an aerosol generating device, which is preferably reusable, in cooperation with a cartridge, which is preferably disposable. In FIG. 1, the system is an electrically operated smoking system. The smoking system 101 comprises a housing 103, having a first end which is the cartridge 105 and a second end which is the device 107. In the device, there is provided an electric power supply in the form of battery 109 (shown schematically in FIG. 1) and electric circuitry 111 (also shown schematically in FIG. 1). In the cartridge, there is provided a storage portion 113 containing liquid 115, an elongate capillary body 117 and a vaporizer in the form of heater 119. In this embodiment, the heater 119 comprises a coil heater surrounding the capillary body 117. Note that the heater is only shown schematically in FIG. 1. In the exemplary embodiment shown in FIG. 1, one end of capillary body 117 extends into the liquid storage portion 113 and the other end of capillary body 117 is surrounded by the heater 119. The heater is connected to the electric circuitry 111 and battery 109 via connections (not shown), which may pass along the outside of the liquid storage portion 113, although this is not shown in FIG. 1. The aerosol generating system 101 also includes a plurality of air flow vents 121, an air outlet 123 at the cartridge end, and an aerosol forming chamber 125. The air flow route 127 from the air flow vents 121 to the air outlet 123 via the aerosol forming chamber 125 is shown by the dotted arrows.

In use, operation is as follows. Liquid 115 is conveyed by capillary action from the liquid storage portion 113 from the end of the capillary body 117 which extends into the liquid storage portion to the other end of the capillary body 117 which is surrounded by heater 119. When a user draws on the air outlet 123, ambient air is drawn through air flow vents 121. In the embodiment of FIG. 1, a puff detection device in the electric circuitry 111 senses the puff and activates the heater 119. The battery 109 supplies electrical energy to the heater 119 to heat the end of the capillary body 117 surrounded by the heater. The liquid in that end of the capillary body 117 is vaporized by the heater 119 to create a supersaturated vapour. At the same time, the liquid being vaporized is replaced by further liquid moving along the capillary body 117 by capillary action. (This is sometimes referred to as "pumping action".) The supersaturated vapour created is mixed with and carried in the air flow 127 from the air flow vents 121. In the aerosol forming chamber 125, the vapour condenses to form an inhalable aerosol, which is carried towards the air outlet 123 and into the mouth of the user. In the embodiment shown in FIG. 1, the electric circuitry 111 is preferably programmable, and can be used to manage the aerosol generating operation.

FIG. 2 is a cross section along line II-II of FIG. 1. FIG. 2 is schematic in nature. In particular, the components shown are not necessarily to scale either individually or relative to one another. In this embodiment, the aerosol generating 101, the aerosol generating device, and the cartridge have a circular cross section. FIG. 2 shows the housing 103 at the cartridge end, the capillary body 117 and the air flow vents 121. The heater 119 is not shown in FIG. 2 for simplicity. In the embodiment of FIG. 2, there are two sets of three air flow vents 121 equally spaced around the circumference of the aerosol generating device. One set of air flow vents 121 is spaced longitudinally from the other set (see FIG. 1). Each air flow vent 121 is arranged to direct air directly onto the surface of the capillary body 117 as shown by the dotted arrows in FIG. 2. Because the aerosol generating system 101 has a circular cross section, air passing through the air flow vents 121 is directed in a radial direction and substantially perpendicular to the longitudinal axis of the aerosol generating system 101. Because the air flow vents 121 are spaced around the circumference of the aerosol generating system, each air flow vent 121 directs air towards the vicinity of the vaporizer in a different direction from at least some of the other air flow vents 121. The embodiment of FIG. 2 has been found to be advantageous, since high velocity air is directed onto the capillary body surface, and this substantially increases the cooling rate.

FIG. 3 is an alternative cross section along line II-II of FIG. 1. FIG. 3 is schematic in nature. In particular, the components shown are not necessarily to scale either individually or relative to one another. In this embodiment, the aerosol generating system 101 and the aerosol generating device and cartridge have a circular cross section. Just like FIG. 2, FIG. 3 shows the housing 103 at the cartridge end, the capillary body 117 and the air flow vents 121. The heater 119 is not shown in FIG. 3 for simplicity. In the embodiment of FIG. 3, there are two sets of three air flow vents 121 equally spaced around the circumference of the aerosol generating device. One set of air flow vents 121 is spaced longitudinally from the other set (see FIG. 1). Each air flow vent 121 is arranged to direct air in a direction across the surface of the capillary body 117 as shown by the dotted arrows in FIG. 3. Because the aerosol generating system 101 has a circular cross section, air passing through the air flow vents 121 is directed in a tangential direction and substantially perpendicular to the longitudinal axis of the aerosol generating system 101. Because the air flow vents 121 are spaced around the circumference of the aerosol generating device, each air flow vent 121 directs air towards the vicinity of the vaporizer in a different direction from at least some of the other air flow vents 121. The embodiment of FIG. 3 has found to be advantageous, since high velocity air is directed across the surface of the capillary body. This substantially increases the cooling rate while minimising cooling of the heater 119.

Referring to FIGS. 1, 2 and 3, each of the air flow vents 121 comprises a small diameter aperture. When a user draws on the aerosol generating device at the air outlet 123, air is drawn through the air flow vents 121. Because of the small diameter of the air flow vents 121, the air is drawn through at high velocity. The high velocity air jet is drawn through the air flow vents 121 directly into the vicinity of the heater 119. This increases cooling of the supersaturated vapour to form the aerosol. Thus, the high velocity air being directed towards the vicinity of the heater 119 controls formation of the aerosol and, in particular, the particle size of the aerosol. Increased cooling has been found to result in a lower mean aerosol droplet size and a smaller range of aerosol droplet sizes.

Referring to FIGS. 1, 2 and 3, each of the air flow vents 121 comprises an aperture with a small diameter or cross section. When a user draws on the aerosol generating device at the air outlet 123, air is drawn through the air flow vents. Because of the small cross sectional area of each vent 121, the air is propelled towards the vicinity of the heater 119 and capillary body 117 at high velocity. The high velocity air flow in the aerosol forming chamber 125 increases the cooling rate, which decreases the mean particle size in the aerosol. Preferably, the distance between the air flow vents 121 and the heater 119 and capillary body 117 is small. This means that there is little opportunity for the air to decelerate or to develop complex patterns of turbulence. In this embodiment, the air flow vents 121 are symmetrically arranged around the heater 119 and capillary body 117. This means that the air flow vents 121 direct the air towards the vicinity of the heater 119 and capillary body 117 in more than one direction. The symmetrical arrangement also results in a relatively homogeneous air flow throughout the aerosol forming chamber 125 and approximately equal cooling on all sides of the heater 119. This decreases the range of particle sizes in the aerosol.

In FIGS. 2 and 3, two sets of three air flow vents are provided. However, any suitable number and layout of air flow vents may be provided according to the desired aerosol characteristics and resistance to draw of the aerosol generating device. Moreover, each air flow vent may have a different size or shape or be arranged to direct the air flow in a different direction.

The capillary body 117 may comprise any suitable material or combination of materials which is able to convey the liquid aerosol-forming substrate 115 towards the heater 119. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity so as to be used with different liquid physical properties.

FIG. 4 is a schematic view of another embodiment of an aerosol generating system according to the invention. FIG. 4 is schematic in nature. In particular, the components shown are not necessarily to scale either individually or relative to one another. Although not explicitly shown in FIG. 4, the aerosol generating system comprises an aerosol generating device, which is preferably reusable, in cooperation with a cartridge, which is preferably disposable. In FIG. 4, the system is an electrically operated smoking system. The smoking system 401 comprises a housing 403, having a first end which is the cartridge 405 and a second end which is the device 407. In the device, there is provided an electric power supply in the form of battery 409 (shown schematically in FIG. 4) and electric circuitry 411 (also shown schematically in FIG. 4). In the cartridge, there is provided a storage portion 413 containing liquid 415. The liquid storage portion 413 includes an interior passageway 416, which is lined with a capillary interface 417. In the cartridge, there is further provided a heater 419 which extends into the interior passageway 416 of the liquid storage portion 413 and is preferably in contact with the capillary interface 417. In this embodiment, the heater 419 comprises a coil heater fitting snugly within the interior passageway 416. Note that the heater is only shown schematically in FIG. 4. The heater 419 is connected to the electric circuitry 411 and battery 409 via connections (not shown). In the cartridge end, there is further provided an air inlet pipe 420, which extends into the interior passageway 416 and provides a conduit for the air flow route. The air inlet pipe 420 includes a plurality of air flow vents 421. The aerosol generating system 401 also includes at least one air inlet 422, an air outlet 423 at the cartridge end, and an aerosol forming chamber 425. The air flow route 427 from the air inlets 422, along the air inlet pipe 420, through the air flow vents 421 and to the air outlet 423 via the aerosol forming chamber 425 is shown by the dotted arrows.

In use, operation is as follows. Liquid 415 is conveyed by capillary action from the liquid storage portion 413 from the face of the capillary interface 417 which is in contact with liquid in the liquid storage portion to the face of the capillary interface 417 which is in contact with or adjacent the heater 419. When a user draws on the air outlet 423, ambient air is drawn through the air inlets 422, along the air inlet pipe 420 and through air flow vents 421. In the embodiment of FIG. 5, a puff detection device in the electric circuitry 411 senses the puff and activates the heater 419. The battery 409 supplies electrical energy to the heater 419 to heat the liquid in the capillary interface 417. The liquid in the capillary interface 417 is vaporized by the heater 419 to create a supersaturated vapour. At the same time, the liquid being vaporized is replaced by further liquid moving through the capillary interface 417 from the liquid storage portion 413 by capillary action. The supersaturated vapour created is mixed with and carried in the air flow 427 from the air flow vents 421. In the aerosol forming chamber 425, the vapour condenses to form an inhalable aerosol, which is carried towards the air outlet 423 and into the mouth of the user. In the embodiment shown in FIG. 5, the electric circuitry 411 is preferably programmable, and can be used to manage the aerosol generating operation.

FIG. 5 is a cross section along line V-V of FIG. 4. FIG. 5 is schematic in nature. In particular, the components shown are not necessarily to scale either individually or relative to one another. In this embodiment, the aerosol generating system 401 and the aerosol generating device and cartridge have a circular cross section. FIG. 5 shows the housing 403, the liquid storage portion 413, the interior passageway 416 and the capillary interface 417. The heater 419 is not shown in FIG. 5 for simplicity. FIG. 5 also shows the air inlet pipe 420 extending into the interior passageway 416. In the embodiment of FIG. 5, there are three sets of three air flow vents 421 equally spaced around the circumference of the air inlet pipe 420. Each set of air flow vents 421 is spaced longitudinally from the other sets (see FIG. 1). Each air flow vent 421 is arranged to direct air onto the capillary interface 417 as shown by the dotted arrows in FIG. 4. Because the aerosol generating system 401 has a circular cross section, air passing through the air flow vents 421 is directed in a radial direction and substantially perpendicular to the longitudinal axis of the aerosol generating system 101. Because the air flow vents 421 are spaced around the circumference of the air inlet pipe 420, each air flow vent 421 directs air towards the vicinity of the vaporizer in a different direction from at least some of the other air flow vents 421. The embodiment of FIG. 5 has been found to be advantageous, since high velocity air is directed onto the capillary interface, and this substantially increases the cooling rate.

Referring to FIGS. 4 and 5, each of the air flow vents 421 comprises an aperture with a small diameter or cross section. When a user draws on the air outlet 423, air is drawn through the air flow vents. Because of the small cross sectional area of each vent 421, the air jet is propelled towards the vicinity of the heater 419 and capillary interface 417 at high velocity. The high velocity air flow in the aerosol forming chamber 425 increases the cooling rate, which decreases the mean particle size in the aerosol. Preferably, the distance between the air flow vents 421 and the heater 419 and capillary interface 417 is small. This means that there is little opportunity for the air to decelerate or to develop complex patterns of turbulence. In this embodiment, the air flow vents 421 are symmetrically arranged around the air inlet pipe 420. This means that the air flow vents 421 direct the air towards the vicinity of the heater 419 and capillary body 417 in more than one direction. The symmetrical arrangement also results in a relatively homogeneous air flow throughout the aerosol forming chamber 425 and approximately equal cooling on all portions of the heater 419. This decreases the range of particle sizes in the aerosol.

In FIG. 5, three sets of three air flow vents are provided on the air inlet pipe. However, any suitable number and layout of air flow vents may be provided according to the desired aerosol characteristics and resistance to draw. Moreover, each air flow vent may have a different size or shape or be arranged to direct the air flow in a different direction.

The capillary interface 417 may comprise any suitable material or combination of materials which is able to convey the liquid aerosol-forming substrate 415 towards the heater 419. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity so as to be used with different liquid physical properties.

FIGS. 1 to 5 show embodiments of an aerosol generating system according to the present invention. Many other examples are possible, however. The aerosol generating system simply needs to include a vaporizer for heating the liquid aerosol-forming substrate, a plurality of air flow vents for directing the air in more than one direction towards the vicinity of the vaporizer, and at least one air outlet, and these components may be provided in either the device or in the cartridge. For example, the system need not be electrically operated. For example, the system need not be a smoking system. In addition, the system may not include a heater, in which case another device may be included to heat the liquid aerosol-forming substrate. For example, the configuration of the capillary material may be different. For example, a puff detection system need not be provided. Instead, the system could operate by manual activation, for example the user operating a switch when a puff is taken. For example, the overall shape and size of the housing could be altered.

Preferably, the cartridge is disposable and is arranged to cooperate with an aerosol generating device which is reusable. The cartridge may be refilled or replaced when the liquid is used. Thus, when the liquid aerosol-forming substrate in the cartridge has been used up, the cartridge may be disposed of and replaced with a new cartridge, or the empty cartridge may be refilled. However, the aerosol generating device may not be designed to operate in conjunction with a separate cartridge. Instead, the aerosol generating device may include or receive a liquid aerosol-forming substrate in a storage portion and comprise a vaporizer for heating the liquid aerosol-forming substrate to form the aerosol, the plurality of air flow vents, and at least one air outlet. Additionally, the aerosol generating device may comprise an electric power supply and electric circuitry In one particular embodiment, the aerosol generating device is a portable smoking device with a size comparable to a conventional cigar or cigarette. The smoking device may have a total length between approximately 30 mm and approximately 150 mm. The smoking device may have an external diameter between approximately 5 mm and approximately 30 mm. In that embodiment, each air flow vent may have a diameter less than or approximately equal to 0.4 mm. In one embodiment, in which a puff lasts approximately 2 s and has a total puff volume of 55 ml (that is a puff flow rate of approximately 27.5 milliliters per second), the high air flow velocity through the air flow vents may be 10 ms$^{-1}$ or between 10 ms$^{-1}$ and 30 ms$^{-1}$. The characteristics of the aerosol produced by the aerosol generating device will depend on the liquid aerosol-forming substrate. The aerosol may have a mean particle size of less than approximately 1.5 microns or, more preferably, less than approximately 1.0 microns. In one example in which the aerosol-forming substrate is propylene glycol, the aerosol may have a mean particle size of less than approximately 0.7 microns.

As discussed above, according to the invention, the aerosol generating device, cartridge or system includes air flow vents which result in a high velocity air flow in the vicinity of the vaporizer. This results in increased cooling leading to a smaller mean particle size, more homogenous air flow leading to a smaller range of particle sizes in the aerosol, and faster aerosol formation leading to a potentially smaller aerosol generating device or system. Embodiments of the porous barrier have been described with reference to FIGS. 1 to 5. Features described in relation to one embodiment may also be applicable to another embodiment.

The invention claimed is:

1. An aerosol generating device, comprising:
   a vaporizer configured to heat an aerosol-forming substrate;
   a plurality of air flow vents; and
   at least one air outlet,
   the plurality of air flow vents and the at least one air outlet being arranged to define an air flow route between the plurality of air flow vents and the at least one air outlet,
   wherein each of the plurality of air flow vents is an air inlet vent providing a first conduit for ambient air to be drawn into the aerosol generating device and being arranged to direct the air towards the vicinity of the vaporizer in a direction across a surface of the vaporizer and substantially perpendicular to a longitudinal axis of the device so as to manage particle size in an aerosol, and
   wherein each of the air inlet vents has a diameter of less than or equal to 0.4 mm.

2. The aerosol generating device according to claim 1, wherein the air inlet vents direct the air in more than one direction.

3. The aerosol generating device according to claim 1, wherein at least one of the plurality of air flow vents includes a deviated portion.

4. The aerosol generating device according to claim 1, further comprising a housing, wherein the air inlet vents are formed in the housing.

5. The aerosol generating device according to claim 1, wherein, for a flow rate of 27.5 milliliters per second through the at least one air outlet, an air flow velocity through each of the air inlet vents is between 10 meters per second and 30 meters per second.

6. The aerosol generating device according to claim 1, further comprising:
   a storage portion configured to store the aerosol-forming substrate; and
   an elongate capillary body configured to convey the aerosol-forming substrate from the storage portion towards the vaporizer, the capillary body having a first end extending into the storage portion and a second end opposite the first end,
   wherein the vaporizer is arranged to heat the aerosol-forming substrate in the second end of the capillary body.

7. The aerosol generating device according to claim 1, further comprising a secondary air inlet and an air flow sensor configured to measure air flow through the secondary air inlet, wherein a secondary air flow route is defined between the secondary air inlet and the at least one air outlet.

8. A cartridge, comprising:
   a storage portion configured to store an aerosol-forming substrate;
   a vaporizer configured to heat the aerosol-forming substrate;
   a plurality of air flow vents; and
   at least one air outlet,
   the plurality of air flow vents and the at least one air outlet being arranged to define an air flow route between the plurality of air flow vents and the at least one air outlet,
   wherein each of the plurality of air flow vents is an air inlet vent providing a first conduit for ambient air to be drawn into the cartridge and being arranged to direct the air towards the vicinity of the vaporizer in a direction across a surface of the vaporizer and substantially perpendicular to a longitudinal axis of the cartridge so as to manage particle size in an aerosol, and
   wherein each of the air inlet vents has a diameter of less than or equal to 0.4 mm.

9. The cartridge according to claim 8, wherein the air inlet vents direct the air in more than one direction.

10. The cartridge according to claim 8, further comprising a housing, wherein the air inlet vents are formed in the housing.

11. The cartridge according to claim 8, wherein, for a flow rate of 27.5 milliliters per second through the at least one air outlet, an air flow velocity through each of the air inlet vents is between 10 meters per second and 30 meters per second.

12. The cartridge according to claim 8, wherein the vaporizer comprises an electric heater configured to heat the aerosol-forming substrate, the electric heater being connectable to an electric power supply.

13. An aerosol generating system, comprising:
   a vaporizer configured to heat an aerosol-forming substrate;
   a plurality of air flow vents; and
   at least one air outlet,
   the plurality of air flow vents and the air outlet being arranged to define an air flow route between the plurality of air flow vents and the air outlet,
   wherein each of the plurality of air flow vents is an air inlet vent providing a first conduit for ambient air to be drawn into the aerosol generating system and being arranged to direct air towards the vicinity of the vaporizer and substantially perpendicular to a longitudinal axis of the system so as to manage particle size in an aerosol,
   wherein the plurality of air flow vents direct air towards the vicinity of the vaporizer in more than one direction, and
   wherein each of the plurality of air flow vents has a diameter of less than or approximately equal to 0.4 mm.

* * * * *